United States Patent [19]

Wang et al.

[11] Patent Number: 5,648,524
[45] Date of Patent: Jul. 15, 1997

[54] METHOD FOR THE PREPARATION OF 3-BENZYLTHIO-2-ALKYLPROPIONIC ACID AND ITS DERIVATIVES

[75] Inventors: Shin-Shin Wang, Hsinchu; Hui-Ping Tsai, Changhua Hsien, both of Taiwan

[73] Assignee: Industrial Technology Research Institute, Hsinchu, Taiwan

[21] Appl. No.: 578,508

[22] Filed: Dec. 26, 1995

[51] Int. Cl.$^6$ .................................................. C07C 321/00
[52] U.S. Cl. ........................................................... 562/426
[58] Field of Search ............................................... 562/426

[56] References Cited

U.S. PATENT DOCUMENTS

| | | | |
|---|---|---|---|
| 4,105,776 | 8/1978 | Ondetti | 424/274 |
| 4,154,580 | 5/1979 | Ondetti | 424/267 |

OTHER PUBLICATIONS

Advance Organic Chemistry; Jerry March, 3rd Edition, pp. 320–322 and 687–688 1985.

*Primary Examiner*—Samuel Barts
*Attorney, Agent, or Firm*—Darby & Darby

[57] ABSTRACT

A method is provided for the preparation of derivative of 3-benzylthio-2-alkylpropionic acid of formula (I):

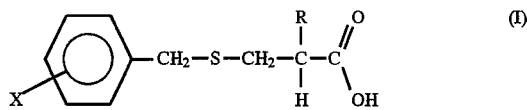

wherein X is independently selected from hydrogen, $C_1$–$C_6$ alkyl or $C_1$–$C_6$ alkoxyl, and R is independently selected from hydrogen or $C_1$–$C_{10}$ alkyl. An alkyl acrylic acid of formula (III):

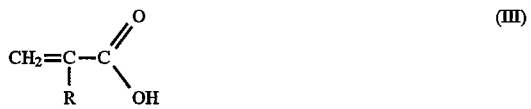

wherein R is as defined above, is reacted with a substituted α-toluenethiol of formula (II):

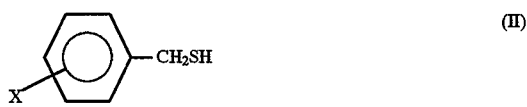

wherein X and R are as defined above, at a stoichiometric mole ratio and in the presence of quaternary ammonium salts or quaternary phosphonium salts serving as phase transfer catalysts at a temperature ranging from 100°–150° C.

Derivatives of 3-benzylthio-2-alkylpropionic acid are obtained in high yield and high purity.

8 Claims, No Drawings

METHOD FOR THE PREPARATION OF 3-BENZYLTHIO-2-ALKYLPROPIONIC ACID AND ITS DERIVATIVES

BACKGROUND OF THE INVENTION

1. Field of the Invention

The present invention relates to the synthesis of 3-benzylthio-2-alkylpropionic acids and their derivatives.

2. Description of the Prior Art 3-benzylthio-2-methylpropionic acids are important intermediates for the synthesis of captopril and alacepril, orally active inhibitors of angiotension converting enzymes used in treating hypertension and cardiac failure.

A method for preparing 3-benzylthio-2-methylpropionic acids and their derivatives has been disclosed in Candian patent No. 1,103,256. Said method includes adding p-methoxy-α-toluene thiol to an aqueous solution of methacrylic acid in NaOH, followed by heating on a steam bath. The yield of the product, 3-[{4-methoxyphenyl)methylthio]-2-methylpropionic acid was reported as 23%. Accordingly, a method for preparing 3-benzylthio-2-methylpropionic acids in high yield is needed in the art.

SUMMARY OF THE INVENTION

It has been found by the inventors that 3-benzylthio-2-methyl propionic acids are obtained in high yield by adding methacrylic acid to an aqueous solution containing α-toluenethiol and quaternary ammonium salts or quaternary phosphonium salts serving as phase transfer catalyst in NaOH solution.

The present invention relates to a method for the preparation of derivatives of 3-benzylthio-2-alkylpropionic acid of the formula:

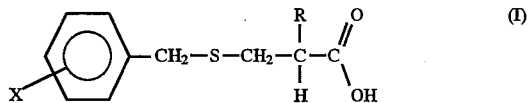

wherein X is independently selected from hydrogen, $C_1$–$C_6$ alkyl or $C_1$–$C_6$ alkoxyl, and R is independently selected from hydrogen or $C_1$–$C_{10}$ alkyl.

According to the invention, an alkyl acrylic acid of formula (III):

wherein R is as defined above, is reacted with a substituted α-toluenethiol of formula (II):

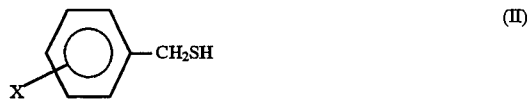

wherein X is as defined above, at a stoichiometric mole ratio, in the presence of quaternary ammonium salts or quaternary phosphonium salts serving as phase transfer catalysts at a temperature ranging from 100°–150° C.

DETAILED DESCRIPTION OF THE INVENTION

Suitable but non-limiting examples of the phase transfer catalysts include tetraethylammonium chloride, tetrabutylammonium bromide, benzyltriethylammounim chloride, benzyltriphenylphosphonium chloride, and tetrabutylphosphonium bromide. The amount of the added phase transfer catalysts is about 0.005–0.5 molar ratio, preferably 0.01–0.1 molar ratio based on the amount of the substituted α-toluenethiol.

In practicing the invention, an aqueous solution containing substituted α-toluenethiol and quaternary ammonium salts or quaternary phosphonium salts in NaOH is first prepared. The resultant aqueous solution is then heated to about 80° C. to 85° C. with agitation. A stoichiometric amount of alkyl acrylic acid is then added. Preferably the alkylacrylic acid is added dropwise within a predetermined time period. Upon completion of the addition, the reaction mixture is heated to 100°–150° C., preferably 125° C., and maintained under reflux for from 15 to 20 hours.

When the reaction reaches completion, as determined by gas chromatgraph or other suitable method, the 3-benzylthiol-2-alkylpropionic acid is extracted from the reaction mixture and purified by conventional procedures. For example, the reaction mixture may be extracted with suitable organic solvents such as ethyl acetate or dichloromethane and the extract is washed with water. Thereafter, the extract is dried over a suitable drying agent such as anhydrous sodium sulfate. Removal of the drying agent and solvent gives 3-benzylthio-2-alkylpropionic acid in yields generally above 90% and with purities typically exceeding 95%.

The following examples illustrate the invention but does not serve to limit its scope.

EXAMPLE 1: THE SYNTHESIS OF 3-BENZYLTHIO-2-METHYLPROPIONIC ACID

To a 25 mL three-necked reaction flask, 3.55 mL (0.03 mole) of α-toluenethiol, 0.58 g ($1.5 \times 10^{-3}$ mole) of benzyl triphenyl phosphonium chloride and 15 mL (0.03 mole) of 2N NaOH solution were added. The resulting solution was heated to 82° C. with agitation for one hour. Thereafter, 2.3 mL (0.027 mole) of methacrylic acid was added dropwise over a 30 minute period to the preheated mixture, and the reaction mixture was heated to 125° C. and maintained under reflux for 18 hours.

After cooling, the alkaline water layer was washed with ethyl acetate (2×20 mL), and acidified with 3N hydrochloric acid (12 mL) to a pH vlaue of 1. The acidified water layer was then extracted with dicholormethane(3×20 mL) and collected. The collected dichloromethane layer was then extracted with 10% sodium hydrogen carbonate solution until no target product was found in the dichloromethane layer (as determined by GC) and the dichloromethane layer was discarded. Ten percent sodium hydrogen carbonate solution was then acidified with 3 N hydrochloric acid solution to a pH value of 1, and extracted with dichloromethane (3×15 mL). The resultant dichloromethane layer was washed with water, dried over anhydrous $Na_2SO_4$, filtered, and concentrated under vacuum to give 5.2038 g of a colorless liquid product (91.8% yield). The purity was 100% as determined by GC.

$^1$H NMR ($CDCl_3$):δ 11.2 (br, 1H), 7.2–7.4 (m, 5H), 3.7 (s,2H), 2.74 (dd, 1H, J=13 & 7.1 Hz), 2.63 (m, 1H), 2.45 (dd, 1H, J=13 & 6.6 Hz), 1.21 (d, 3H, J=6.8 Hz); $^{13}$C NMR ($CDCl_3$):δ 181.2, 137.8, 128.7, 128.3, 126.9, 39.6, 36.4, 34.0, 16.4.

EXAMPLE 2: THE SYNTHESIS OF 3-[(4-METHOXYPHENYL)METHYLTHIO]-2-METHYLPROPIONIC ACID

To a 25 mL three-necked reaction flask, 4.2 mL (0.03 mole) of p-methoxy-α-toluenethiol, 0.58 g ($1.5 \times 10^{-3}$ mole)

of benzyltriphenyl phosphonium chloride and 15 mL (0.03 mole) of 2N NaOH solution were added. The resulting solution was heated to 82° C. with agitation for one hour. Thereafter, 2.56 mL (0.03 mole) of methacrylic acid were added dropwise to the preheated mixture over a 30 minute period, and the reaction mixture was heated to 125° C. and maintained under reflux for 18 hours.

After cooling, the alkaline water layer was washed with ethyl acetate (2×20 mL), and acidified with 3N hydrochloric acid (12 mL) to a pH vlaue of 1. The acidified water layer was then extracted with dicholormethane (3×20 mL), and collected. The collected dichloromethane layer was then washed with saturated sodium choloride solution, dried over anhydrous $Na_2SO_4$, filtered, and concentrated under vacuum to give 5.42 g of a crude product (yield 75.3%, purity 93.2%).

2 g of crude product was then recrystallized with 10 mL of cyclohexane to form a white solide. After drying in an oven at 60° C., 1.6328 g of 3 [(4-methoxyphenyl) methylthio]-2-methylpropionic acid was obtained (yield 81.6%, purity 100%). $^1H$ NMR $(CDCl_3)$:δ 9.6 (br, 1H), 7.22 (d,2H, J=14.5 Hz), 6.85 (d, 2H, J=14.5 Hz), 3.8 (s,3H), 3.68 (S, 2H), 2.7 (dd, 1H, J=13 & 7.1 Hz), 2.66 (m, 1H), 2.5 (dd, 1H, J=13 &6.6 Hz), 1.21 (d, 3H, J=6.8 Hz); $^{13}C$ NMR $(CDCl_3)$:δ 181.5, 158.6, 129.9, 113.9, 55.2, 39.7, 36.0, 34.0, 16.6.

EXAMPLES 3–6

The same procedures as in Example 1 were repeated except that phase transfer catalysts as indicated in Table 1 were used. The yields and purities of the resulting 3-benzylthio-2-methylpropionic acid acids are summarized in Table 1 below.

TABLE 1

| Ex. No. | phase transfer catalyst | Yield (%) | Purity (%) |
|---|---|---|---|
| 3 | tetraethyl ammonium chloride | 90 | 100 |
| 4 | tetrabutyl ammonium bromide | 90 | 100 |
| 5 | benzyltriethyl ammonium chloride | 91 | 100 |
| 6 | tetrabutyl phosphonium bromide | 92 | 100 |

Note:
*purity is determined by GC ratio

EXAMPLES 7–10

The same procedures as in Example 2 were repeated except that phase transfer catalysts as indicated in Table 2 were used. The yields and purities of the resulting 3-[(4-methoxyphenyl)methylthio)-2-methylpropionic acid are summarized in Table 2 below.

TABLE 2

| Ex. No. | phase transfer catalyst | Yield (%) | *Purity (%) |
|---|---|---|---|
| 7 | benzyltriethyl ammonium chloride | 76.2 | 98 |
| 8 | tetrabutyl ammonium bromide | 75.5 | 97.3 |
| 9 | tetraethyl ammonium chloride | 71.6 | 96.6 |
| 10 | tetrabutyl phosphonium bromide | 76.5 | 98 |

Note:
*purity is determined by GC ratio

EXAMPLE 11: THE SYNTHESIS OF 3-BENZYLTHIO PROPIONIC ACID

By substituting acrylic acid for methacrylic acid in the procedures of Example 1, 3-benzylthio propionic acid was obtained and the yield was 92%.

What is claimed is:

1. A method for the preparation of derivatives of 3-benzylthio-2-alkylpropionic acid of the formula:

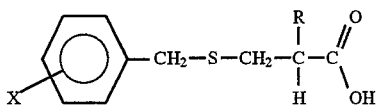

wherein X is independently selected from hydrogen, $C_1$–$C_6$ alkyl or $C_1$–$C_6$ alkoxyl, and R is independently selected from hydrogen or $C_1$–$C_{10}$ alkyl, comprising: reacting in an aqueous solution including a phase transfer catalyst, a substituted α-toluenethiol of formula:

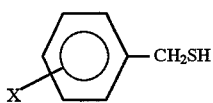

wherein X is as defined above, with an alkyl acrylic acid of formula:

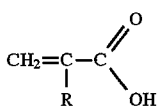

wherein R is as defined above, said phase transfer catalyst is selected from quaternary ammonium salts and quaternary phosphonium salts.

2. The method of claim 1, wherein the reaction temperature is from about 100°–150° C.

3. The method of claim 2, wherein the reaction temperature is about 125° C.

4. The method of claim 1, wherein the reaction is maintained under reflux.

5. The method of claim 1, wherein said quaternary ammonium salts are selected from tetraethylammonium chloride, tetrabutylammonium bromide, and benzyltriethylammounim chloride.

6. The method of claim 1 wherein said quaternary phosphonium salts are selected from benzyltriphenylphosphonium chloride, and tetrabutylphosphonium bromide.

7. The method of claim 1, wherein the molar ratio of the alkyl acrylic acid to the substituted α-toluenethiol is about 1:1.

8. The method of claim 1, wherein the amount of the phase transfer catalyst to the substituted α-toluenethiol is about 0.005–0.5 molar ratio.

* * * * *